United States Patent [19]

Meguro et al.

[11] Patent Number: 5,545,190
[45] Date of Patent: Aug. 13, 1996

[54] SUPER-COMPACT ELECTRIC THERMAL TREATMENT DEVICE

[75] Inventors: Yasuo Meguro, Hino; Hiroshi Yabu, Fuchu, both of Japan

[73] Assignee: Kabushiki Kaisya Advance, Tokyo, Japan

[21] Appl. No.: 356,797

[22] Filed: Dec. 13, 1994

Related U.S. Application Data

[63] Continuation of Ser. No. 996,437, Dec. 24, 1992, abandoned.

[30] Foreign Application Priority Data

Dec. 26, 1991 [JP] Japan ............... 3-112154 U

[51] Int. Cl.⁶ ........................................ A61F 7/00
[52] U.S. Cl. ........................................ 607/96
[58] Field of Search ............... 607/46, 96, 98–99; 219/527

[56] References Cited

U.S. PATENT DOCUMENTS

| | | | |
|---|---|---|---|
| 4,381,009 | 4/1983 | Del Bon | 128/399 |
| 4,572,190 | 2/1986 | Azam et al. | 128/399 |
| 4,585,002 | 4/1986 | Kissin | 128/399 |
| 4,733,056 | 3/1988 | Kojima et al. | 219/543 |
| 4,878,493 | 11/1989 | Pasternak et al. | 607/99 |
| 4,942,884 | 7/1990 | Ichinomiya et al. | 607/98 |

FOREIGN PATENT DOCUMENTS

| | | |
|---|---|---|
| 0243171 | 10/1987 | European Pat. Off. . |
| 1445514 | 6/1966 | France . |
| 2931610 | 2/1981 | Germany . |
| 62-166567 | of 1987 | Japan . |
| 3-8223 | of 1991 | Japan . |
| 1171095 | 5/1964 | Netherlands . |

*Primary Examiner*—Lee S. Cohen
*Assistant Examiner*—Herman J. Robinson
*Attorney, Agent, or Firm*—Finnegan, Henderson, Farabow, Garrett & Dunner

[57] ABSTRACT

A super-compact electric thermal treatment device enabling a patient to correct a treatment temperature comprises a small-capacity compact battery, a heating element, a pulse supplier for intermittently supplying electric energy from the small-capacity compact battery to the heating element, and a corrector for correcting an amount of supply from the pulse supplier manually and variably.

3 Claims, 5 Drawing Sheets

SUPER-COMPACT ELECTRIC THERMAL TREATMENT DEVICE

This application is a continuation of application Ser. No. 07/996,437, filed Dec. 24, 1992, now abandoned.

BACKGROUND OF THE INVENTION

1. Field of the Invention

The present invention relates to a super-compact electric thermal treatment device.

2. Description of the Related Art

A compact electric thermal treatment device applies heat to a lesion of a living body by repeatedly discontinuing electrical coupling between a button, seal, or coin type battery having a very small capacity and a heating element that performs electrothermal conversion. In this kind of compact electric thermal treatment device, it is unavoidable to use a combination of a very small capacity battery and a heating element having a resistance or a heavy load of several ohms to several tens of ohms.

When a heavy load is connected to the above kind of very small capacity battery, a heating element generates heat to provide a satisfactory heating effect. The capacity of a very small capacity battery greatly varies from product to product. Moreover, the variation cannot be ignored in terms of the internal resistance of the heating element. This results in a great difference in heating temperature among products despite the same construction and same parts. This has been a significant drawback.

Therefore, materialization of a super-compact electric thermal treatment device or an electric thermal treatment device using a very small capacity battery, in which a user can select a heating temperature freely to receive an effective treatment, has been awaited.

SUMMARY OF THE INVENTION

Accordingly, an object of the present invention is to provide a super-compact electric thermal treatment device in which a manual and variable correcting means for correcting a heating temperature manually and variably is incorporated so that a user can select a treatment temperature properly.

To achieve the foregoing object, a super-compact electric thermal treatment device according to the present invention adopts the technical construction mentioned below. Specifically, the super-compact electric thermal treatment device comprises a small capacity battery, a heating element for electrothermal conversion, a pulse supplying means for supplying electric energy from the small capacity compact battery to the heating element intermittently, and a correcting means for correcting the amount of the supply from the pulse supplying means manually and variably.

DETAILED DESCRIPTION OF THE PREFERRED EMBODIMENTS

Embodiments of a super-compact electric thermal treatment device according to the present invention will now be described with reference to the drawings.

Figure 1:
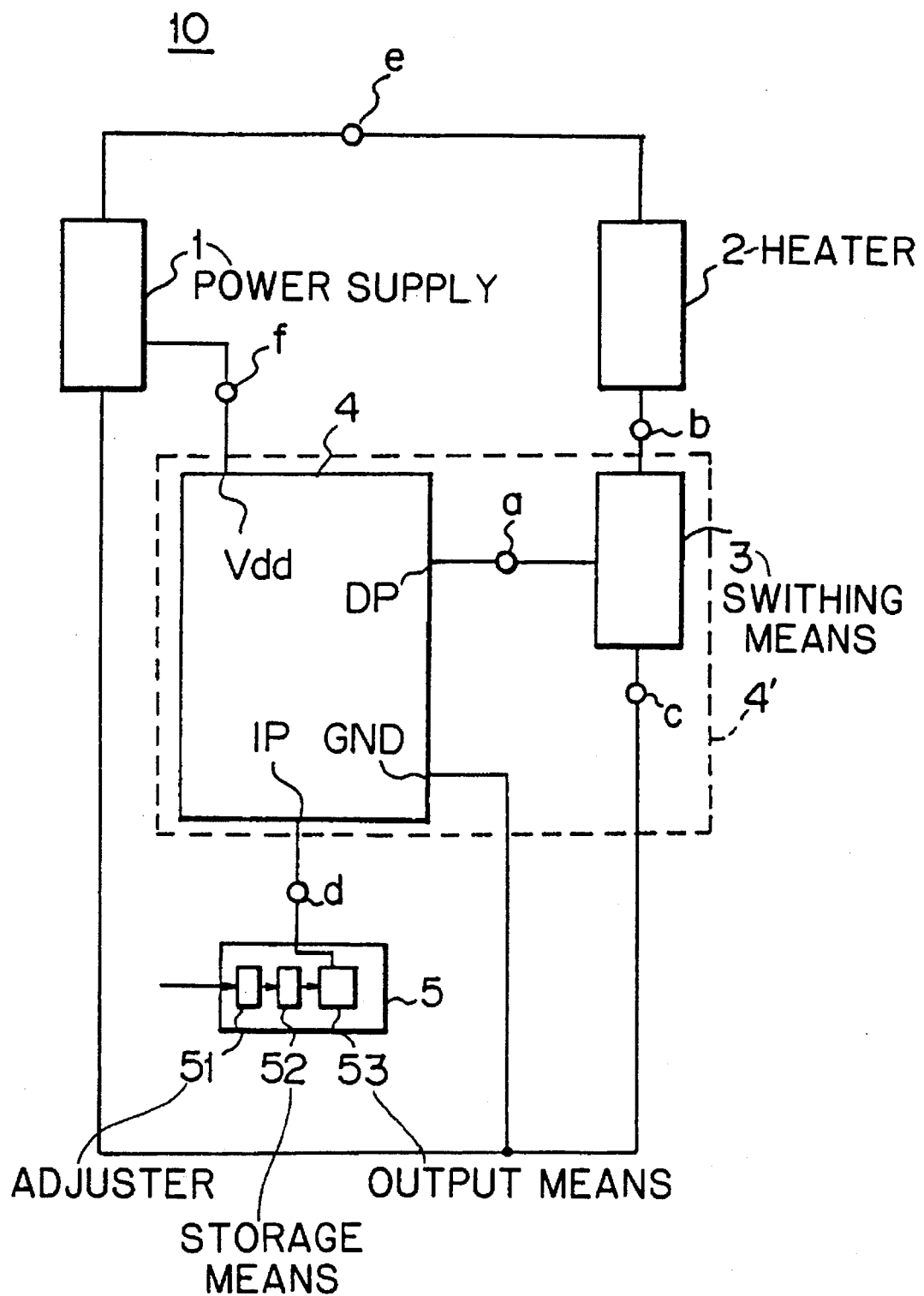
FIG. 1 is a block diagram showing an embodiment of the present invention.

FIG. 1 is a block diagram showing an embodiment of a super-compact electric thermal treatment device according to the present invention. In FIG. 1, a super-compact electric thermal treatment device 10 comprises a small-capacity compact power supply 1, a heating element 2 for electrothermal conversion, a pulse supplying means 4 for intermittently supplying electric energy from the small-capacity power supply 1 to the heating element 2, and a correcting or adjusting means 5 for correcting or adjusting the amount or duration of the supply from the pulse supplying means 4 both manually and variably.

In the thermal treatment device 10 according to the present invention, the manual and variable correcting means 5 comprises an adjuster 51 for manually adjusting a heating temperature for thermotherapy, a storage means 52 for electrically and mechanically storing an adjustment value adjusted by the adjuster 51, and an output means 53 for outputting information stored by the storage means to the pulse supplying means.

The adjuster 51 employed for this invention is a knob or a button that is turned or operated by a patient or wearer of the device. The storage means 52 stores a quantity of drive by which the adjuster such as a knob or a button is driven. The storage means 52 can be, for example, a variable resistor or a sliding switch.

Electric storage in the present invention means storage using a digital memory means such as a resistor and a memory, and an analog storage means such as a capacitor. These electric storage means are united with arithmetic logic units in the form of, for example, a one-chip microcomputer, and may be controlled by programs. In the electric storage, once a storage time is varied, the time may be valid only during one thermal treatment or may remain valid until the battery is replaced.

In FIG. 1, a power supply 1 is made up of button, coin, or sheet type primary and secondary batteries and a DC/DC converter having a voltage transformation function. The outputs of the batteries are fed to a terminal e and the output of the DC/DC converter is fed to a terminal f.

The heating element 2 such as a heater is a Nichrome wire, a tungsten wire, or other filament type heating element. Alternatively, the heating element 2 is a ceramic chip on which silver and palladium is printed and burnt. Numeral 3 in FIG. 1 denotes a switching means that is realized with a FET or a relay. The switching means 3 is used to turn on or off electrical coupling between terminals b and c in response to a 1 or 0 fed as a pulse to the terminal a.

The pulse supplying means 4 is, for example, a pulse oscillator, and outputs pulses with a given pulse width and pulse duration. Each of the given values covers a time-sequential change. In the present invention, the switching means 3 may be incorporated in the pulse supplying means 4. The correcting means 5 includes, as mentioned above, a manual and variable adjustment function.

Next, the connections of the aforesaid components will be described.

A positive electrode of a power supply 1 is connected to the heater 2 via a terminal e. The other terminal of the heater 2 is connected to the switching means 3 via a terminal b. A terminal c of the switching means 3 is connected to a negative electrode of the power supply 1. A boosted output of the power supply 1 is fed to Vdd of pulse supplying means 4 including a pulse oscillator hereafter pulse osciallator 4 via a terminal f. A pulse output pin DP of the pulse oscillator 4 is connected to a terminal a of the switching means 3. The correcting means 5 is connected to the pulse oscillator 4 via a connection pin IP of the oscillator 4 via a terminal d. A pin GND of the pulse oscillator 4 is connected to the negative electrode of the power supply 1.

Next, the operation will be described.

A power supply 1 supplies a battery output to a heater 2 via a terminal e. A boosted output of the power supply 1 is supplied to a power input pin Vdd of a pulse oscillator 4 via a terminal f.

Figure 2A:
FIGS. 2A, 2b, 3A, 3b, 4A, and 4b are explanatory diagrams for the operation waves of the embodiment shown in FIG. 1.

With the supply, the pulse oscillator 4 starts operating and outputs a drive pulse from a drive pulse output pin DP. FIG. 2a shows an example of drive pulses.

The drive pulses are fed to a switching means 3 via a terminal a. When a drive pulse represents a 1, the switching means 3 electrically couples terminals b and c. When the drive pulse represents a 0, the switching means 3 electrically decouples the terminals b and c.

Figure 2B:

By repeating the above operation, electric energy is supplied intermittently to the heater 2. The temperature of the heater 2 rises gradually as shown in FIG. 2b. Normally, if the outputs of the power supply 1 and heater 2 are as per ratings, a correcting means 5 need not be actuated but thermotherapy can still be carried out satisfactorily. However, as described previously, the outputs of the power supply 1 and heater 2 may deviate from the ratings.

Figure 3A:
Figure 3B:
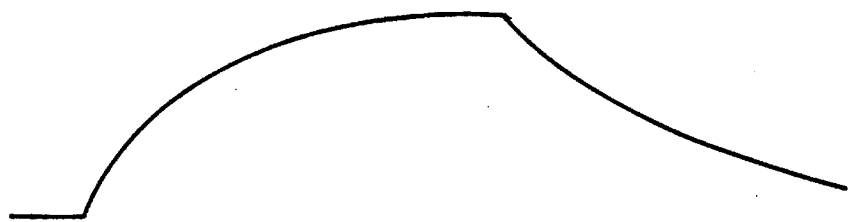
Figure 4A:
Figure 4B:

When a charge or a discharge capacity of a battery is not enough to provide a warm feeling, a patient adjusts the adjuster 51 of the correcting means 5. The correcting means 5 stores an adjustment value and continues to output a signal equivalent to the adjustment value to the pulse oscillator 4. With the adjustment signal, the pulse oscillator 4 outputs a drive pulse having a high on-state duty ratio as shown in FIG. 3a to an output terminal DP. On the contrary, when a charge or a discharge capacity of a battery is so large as to provide too warm a feeling, a patient reverses the adjuster 51 of the correcting means 5. Then, the pulse oscillator 4 outputs drive pulses as shown in FIG. 4a. The heater 2 generates heat according to the pulses. Thus, the heating value is held low.

Figure 5:
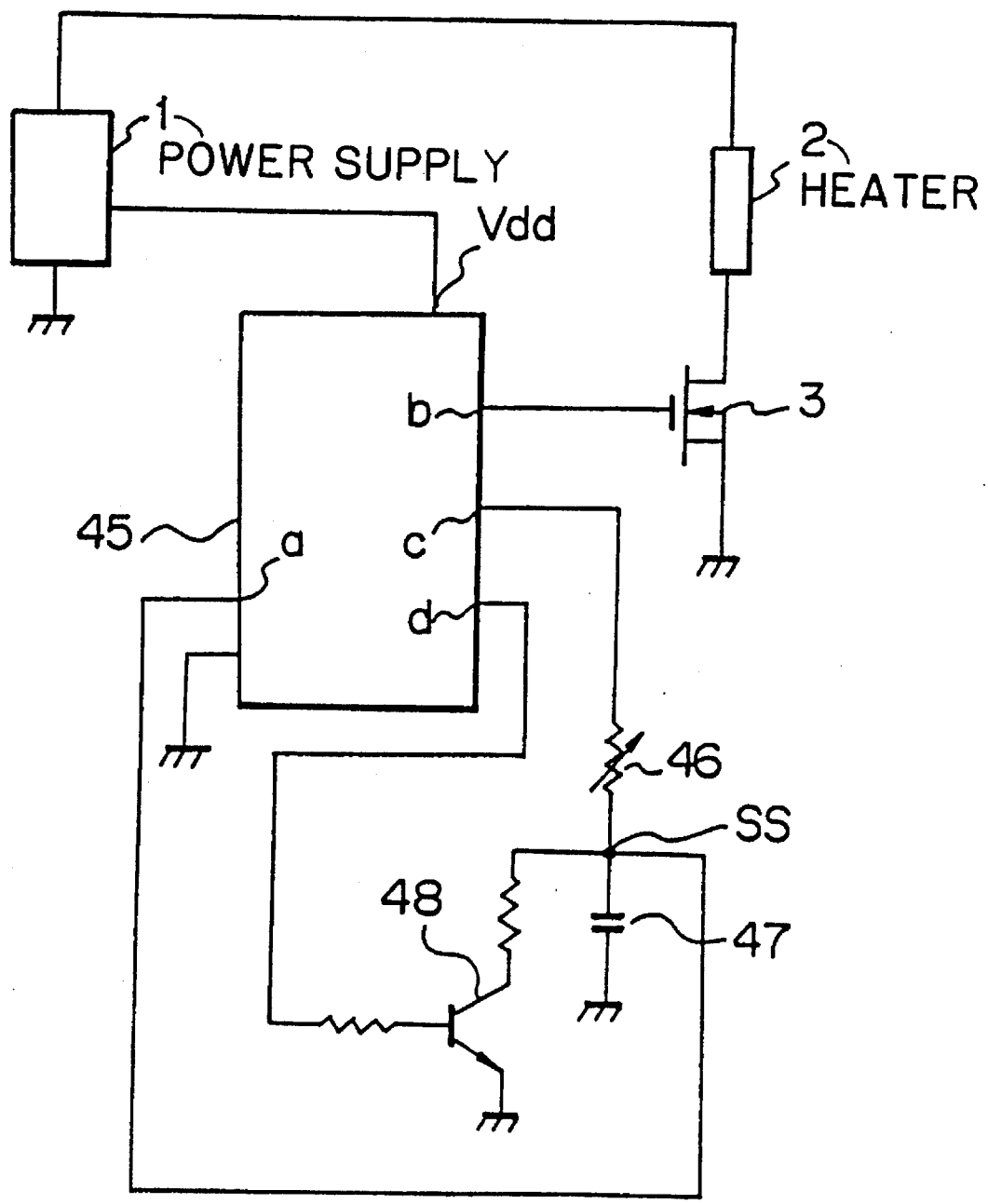
FIG. 5 is a circuit diagram showing other embodiment of the present invention.

Next, a more exemplary embodiment will be described in more detail using FIG. 5.

Reference 1 denotes a power supply, which is made up of a coin type secondary battery and a DC/DC converter.

Reference 2 denotes a heater made by printing and burning silver and palladium on a ceramic substrate.

Reference 3 denotes a switching means realized with an FET.

Reference 45 denotes a one-chip microcomputer acting as a pulse oscillator of a pulse supplying means.

Reference 46 denotes a variable resistor serving as an adjuster. A rotary or sliding type variable resistor is employed. The variable resistor 46 has a knob for manipulating the variable resistor 46.

Reference 47 denotes a capacitor, and 48 denotes a switching transistor.

Next, the connections of the foregoing components will be described.

An output terminal of a battery serving as a power supply 1 is connected to one terminal of a heater 2. An output terminal of a DC/DC converter is connected to a power input pin Vdd of a one-chip microcomputer 45. The other terminal of the heater 2 is connected to a drain of a FET 3. The source of the FET 3 is connected to a minus terminal of the battery serving as the power supply 1. Connecting to the minus terminal of the battery corresponds to grounding. The gate of the FET 3 is connected to an output pin b of the one-chip microcomputer 45. The output pin c of the one-chip microcomputer 45 is connected to one terminal of a variable resistor 46. The other terminal of the variable resistor 46 is connected to one terminal of a capacitor 47 and to an input pin a of the one-chip microcomputer 45. The terminal of the capacitor 47 is connected to a collector of a switching transistor 48. The other terminal of the capacitor 47 and the emitter of the switching transistor 48 are grounded.

The base of the switching transistor 48 is connected to an output pin d of the one-chip microcomputer 45.

Next, the operation will be described.

First, the operation for increasing a heating value of a heater 2 will be described.

A knob of a variable resistor 46 is turned to decrease its resistance. A DC/DC converter of a power supply 1 outputs a battery voltage for actuating a one-chip microcomputer 45. The voltage is supplied to a power pin Vdd of the one-chip microcomputer 45. This places the one-chip microcomputer in an operative state. The one-chip microcomputer 45 outputs pulses shown in FIG. 6a via an output pin c. The variable resistor 46 and capacitor 47 constitute an integrator. Consequently, the voltage at a terminal SS varies as shown in FIG. 6b. A certain threshold is specified for an input pin a of the one-chip microcomputer 45. When the potential at the terminal SS exceeds the threshold, the one-chip microcomputer 45 checks an input at the input pin a and starts feeding pulses to an output pin b. FIG. 6c shows these outputs.

Figure 6A:
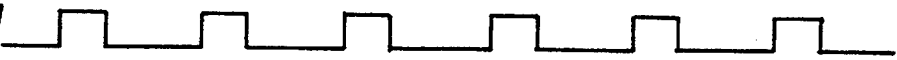
FIGS. 6A, 6b, 6c, 6d, and 7A, 7b, 7c, and 7d are explanatory diagrams for the operation waves of the components in the embodiment shown in FIG. 5.
Figure 6B:
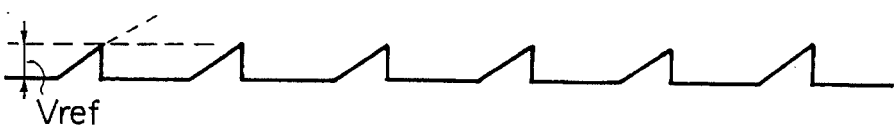
Figure 6C:
Figure 6D:
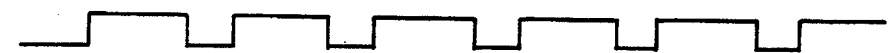

The output at the output pin b falls when the pulse shown in FIG. 6a falls. An output at an output pin d is identical to that at the output pin b. A transistor 48 is on in a period from when the output at the output pin d rises until it falls. Thereby, redundant charge accumulated in a capacitor 47 is discharged.

In a period from when the output at the output pin b rises until it falls, a FET 3 is on. Thereby, current flows to the heater 2. The time from when the output at the output pin b rises until it falls increases as the resistance of the variable resistor 46 decreases. Then, a conducting time during which current flows to the heater 2 extends, resulting in a larger heating value.

Figure 7A:
Figure 7B:
Figure 7C:
Figure 7D:

On the contrary, when the heating value of the heater 2 must be diminished, the knob of the variable resistor 46 is turned to increase the resistance. Thereafter, a operation reverse to the one mentioned above is carried out. Then, the one-chip microcomputer 45 outputs pulses with a smaller pulse width as shown in FIG. 7d. FIG. 7b shows an output voltage wave at the terminal SS shown in FIG. 5. FIG. 7c shows a voltage wave at the output pin d of the one-chip microcomputer 45.

Next, an example of an overall construction based on the aforesaid embodiment of a super-compact electric thermal treatment device according to the present invention will be described in conjunction with FIGS. 8 to 11.

Figure 8:
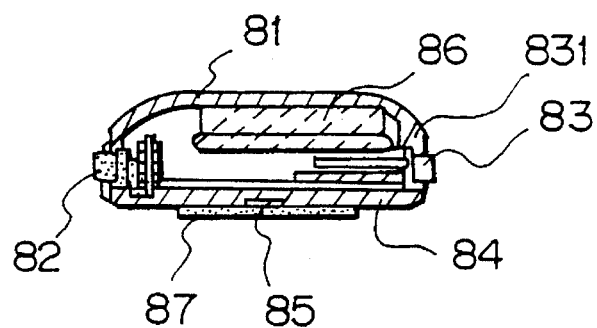
FIG. 8 shows a cross section of an overall construction formed according to an embodiment of the present invention.
Figure 9:
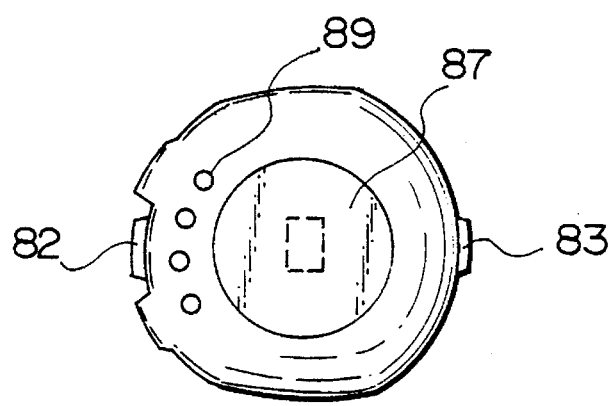
FIG. 9 is a bottom view of the overall construction shown in FIG. 8.
Figure 10:
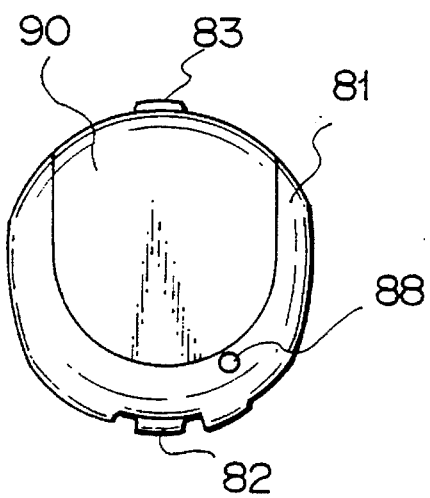
FIG. 10 is a top view of the overall construction shown in FIG. 8.
Figure 11:
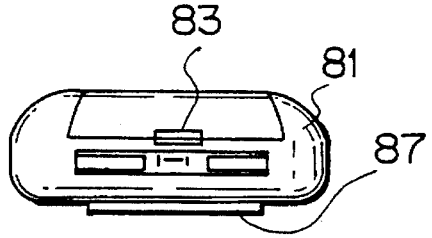
FIG. 11 is a side view of the overall construction shown in FIG. 8.

FIG. 8 shows a cross section of the overall construction. Reference 81 denotes a housing made of a hard plastic. Reference 82 denotes a push or sliding type Start button. The Start button 82 projects from the side of the housing 81.

Reference 83 denotes a knob connected to a sliding type variable resistor. A heating value can be adjusted by sliding the knob. The knob 83 is arranged on the side of the housing 81 opposite from the Start button 82.

Reference 84 denotes an electric circuit board. Electronic circuits shown in FIGS. 1 and 5 are mounted on the electronic circuit board 84. The Start button 82 and sliding type variable resistor 83 are also mounted on the electronic circuit board 84.

Reference 85 denotes a heating element that is made by, for example, printing tungsten on a ceramic plate. The heating element 85 is electrically coupled to the electronic circuit board 84. The heating element 85 is embedded in the bottom of the housing 81 so that it will be exposed from the bottom.

Reference 86 denotes a button or coin type battery. For example, a nickel-cadmium battery is employed.

Reference 87 denotes an adhesive gel member. The adhesive gel member 87 is attached to the bottom of the housing 81 so that it will cover the heating element 85.

Reference 88 denotes an LED. The LED 88 indicates operation.

Reference 89 denotes a charge input terminal for inputting a charge from the battery 86 or an external unit.

Next, an example of a conductive adhesive gel 7 will be presented.

| Ingredient | Content (percentage by weight) |
| --- | --- |
| Alternate copolymer (isobutylene/maleic anhydride) | 24 |
| Dipropylene glycol or propylene glycol | 37 |
| Concentrated glycerin | 9 |
| Sodium chloride | 1 |
| Polyglycerinpolyglycidylether | 4 |
| Sodium hydroxide (pH regulator) | 5 |
| Refined water | 20 |

Preparation: the above ingredients are mixed.

The usage of the super-compact electric thermal treatment device will be described. Fist, the adhesive gel member is brought into contact with a lesion of a living body. Since the overall weight is about several tens of grams, the device will remain adhered to the lesion.

The Start button 82 is pressed, and then the electric circuits on the electric circuit board 84 are driven and electric energy is supplied from the battery 86 to the heating element 85.

Current is supplied to the heating element 85 intermittently. Nevertheless, the temperature of the heating element rises smoothly. When the temperature reaches its peak, if the patient is dissatisfied with the temperature, the patient slides a variable resistor 83 unidirectionally. Similarly to the embodiments described in conjunction with FIGS. 1 to 5, the heat temperature of the heating element 85 rises. After a given time has elapsed, heat generation stops. When the device is reused, since the variable resistor 83 has already been slid, the heat temperature remains satisfactory to the patient.

On the contrary, when the heat temperature of the heating element 85 is too high, the variable resistor 83 is slid in an opposite direction to lower the temperature. When the device is reused, treatment proceeds with a preferred temperature maintained.

As described so far, the present invention provides a compact electric thermal treatment device in which a heating element having a very small electric resistance and a coin or button type battery whose capacity varies from product to product are combined. An adjusting means permitting manual variation, storage, and adjustment of a heating value is incorporated to correct a variation in heating value. Thereby, a preferred heating value is provided all the time.

We claim:

1. A super-compact electric thermal treatment device, comprising:

a small-capacity compact battery;

a heating element for performing electrothermal conversion electrically connected to the battery and having a conducting adhesive material thereon for adhering the device to a user thereof;

a switching means for intermittently switching current flowing from said battery through said heating element;

a pulse supplying means electrically connected to the battery for generating output pulses of a given width and for supplying said output pulses to said switching means to control the intermittent switching of the switching means; and an adjusting means for manually adjusting the pulse width of the output pulses generated by the pulse supplying means to vary the amount of current intermittently supplied from the battery to the heating element and thereby the amount of heat generated by said heating element.

2. The super-compact electric thermal treatment device of claim 1, wherein said heating element includes a ceramic substrate.

3. The super-compact electric thermal treatment device of claim 2, wherein said adjusting means varies an on-state duty ratio of the pulses provided by said pulse supplying means by adjustment of a combination of a variable resistor and a capacitor.

* * * * *